United States Patent [19]

Gronek et al.

[11] Patent Number: 4,585,351

[45] Date of Patent: Apr. 29, 1986

[54] APPARATUS FOR INSPECTING SURFACE MOUNTED COMPONENTS

[75] Inventors: Fred J. Gronek, North Riverside; Raymond M. Taradejna, Bolingbrook; Ray A. Watkins, Aurora, all of Ill.

[73] Assignee: AT&T Technologies, Inc., Berkeley Heights, N.J.

[21] Appl. No.: 534,031

[22] Filed: Sep. 20, 1983

[51] Int. Cl.[4] .......................................... G01N 21/01
[52] U.S. Cl. ..................................... 356/388; 269/73; 356/237
[58] Field of Search ............... 356/237, 388, 394, 397; 269/70, 73, 309, 310

[56] References Cited

U.S. PATENT DOCUMENTS

| | | | |
|---|---|---|---|
| 3,143,791 | 8/1964 | Lanahan et al. | 269/73 |
| 3,471,236 | 10/1969 | Pearson | 356/24 |
| 4,028,728 | 6/1977 | Sharp | 356/237 |
| 4,274,801 | 6/1981 | Herb et al. | 269/73 |
| 4,389,669 | 6/1983 | Epstein et al. | 356/394 |

OTHER PUBLICATIONS

"Manual X-Y Wafer Positioner," Cadwallader, *IBM Technical Disclosure Bulletin*, vol. 25, No. 5, 10/82, p. 2383.
"Integrated Circuit Chip Positioning Tool," Schuelke, *IBM Technical Disclosure Bulletin*, vol. 13, No. 7, 12/70, p. 2115.
"Chip Alignment Probe," Chiou et al., *IBM Technical Disclosure Bulletin*, vol. 12, No. 10, 3/70, p. 1547.

Primary Examiner—R. A. Rosenberger
Attorney, Agent, or Firm—H. St. Julian; M. de Picciotto

[57] ABSTRACT

A hybrid integrated circuit (10), having a plurality of chip carriers (12) mounted thereon, is positioned on a nest (50) of an apparatus (30). An operator, while activating pneumatic switches (58), moves a selected one of the plurality of chip carriers (12) to an inspection site. A sensor plunger (62) detects the presence of the chip carrier (12) and enables a positioning assembly (34), which centers the chip carrier within the inspection site and locks the nest (50), to prevent further movement thereof. A viewing adaptor (70) is then lowered about the selected chip carrier (12) to enable the operator to simultaneously inspect all solder joints (22) positioned beneath the selected chip carrier. Thereafter, the operator releases switch actuator (60) which allows the viewing adaptor (70) to be raised and enables the positioning assembly (34) to unlock the nest (50) so that another chip carrier (12) may be moved to the inspection site for inspection by the operator.

7 Claims, 11 Drawing Figures

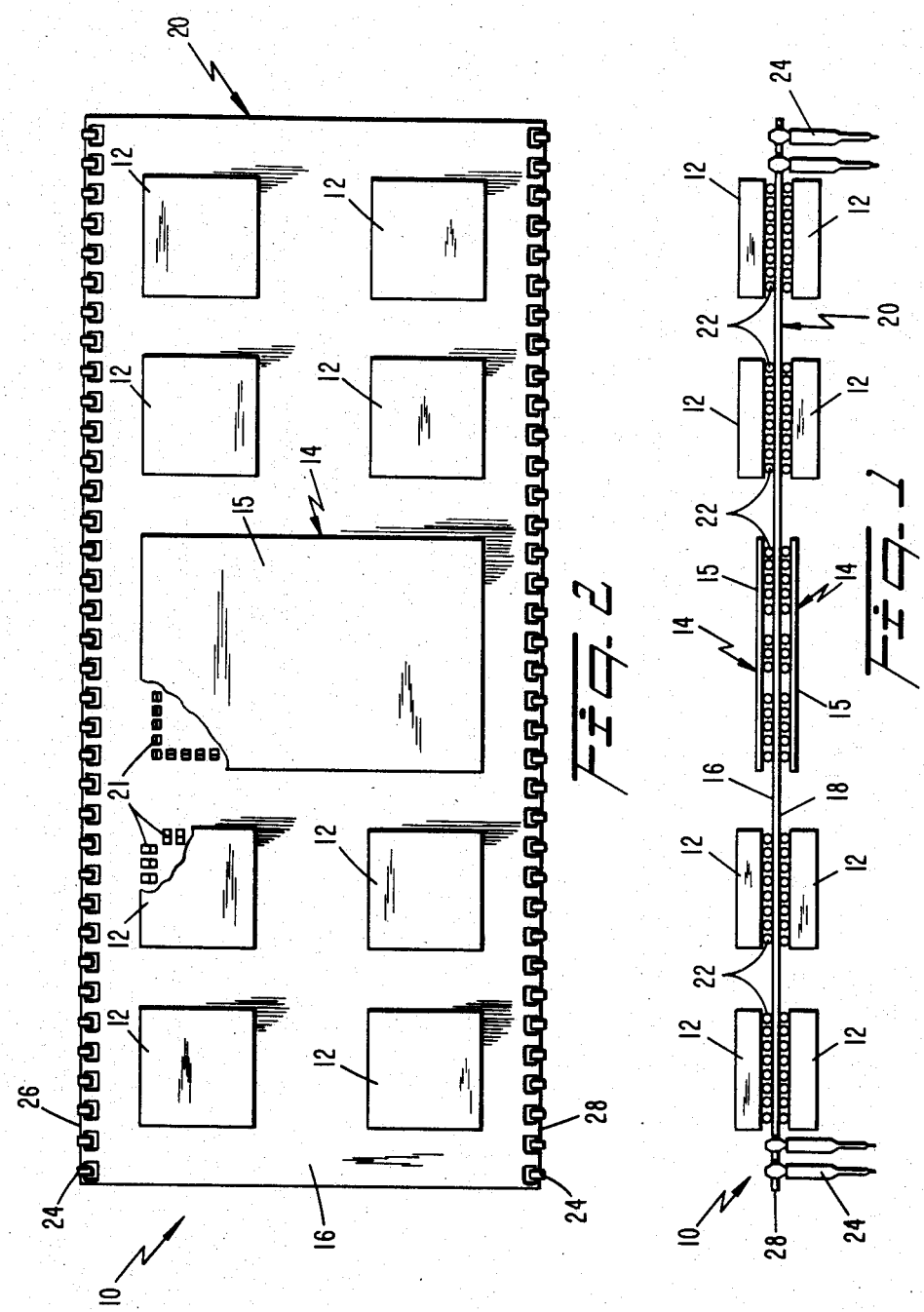

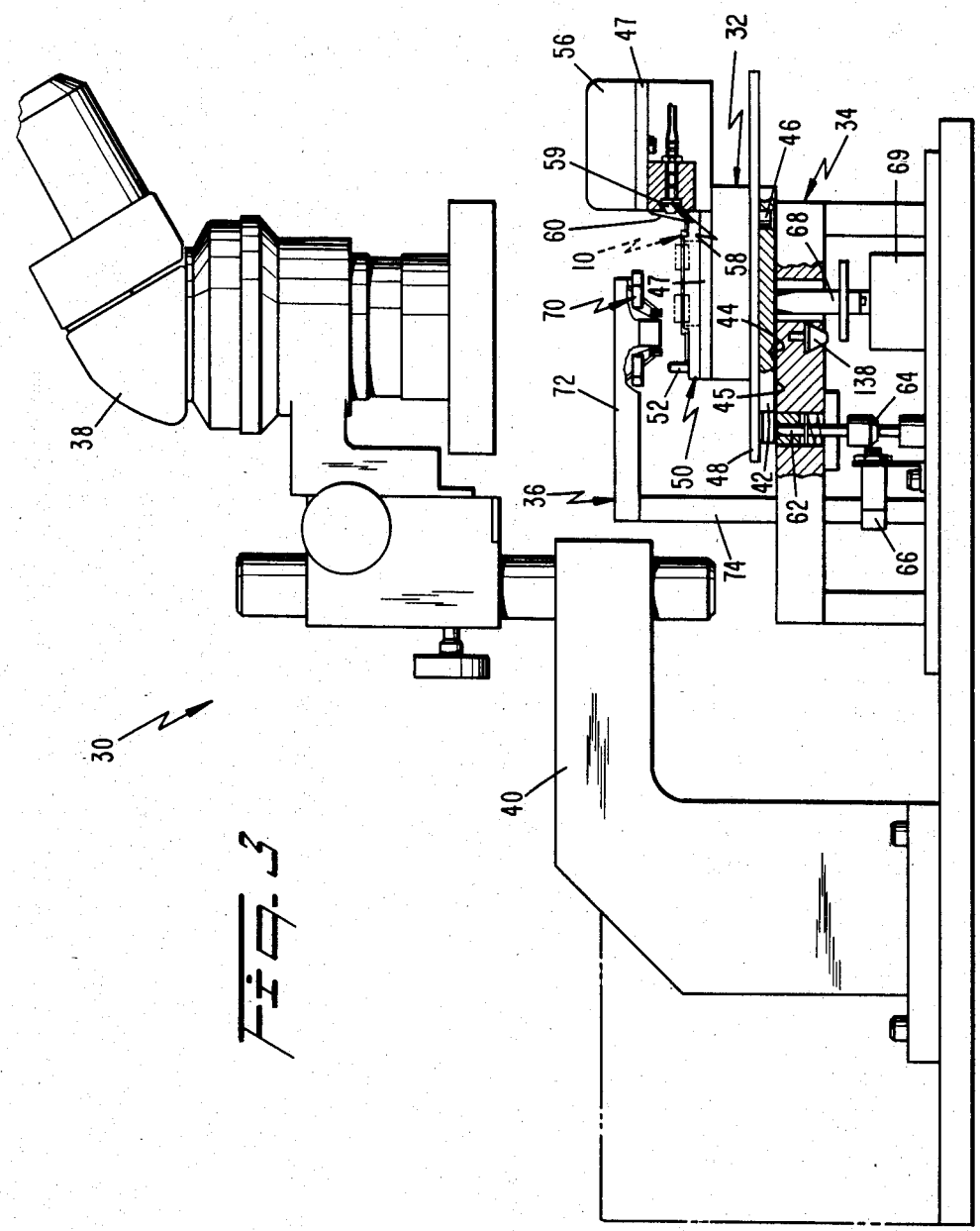

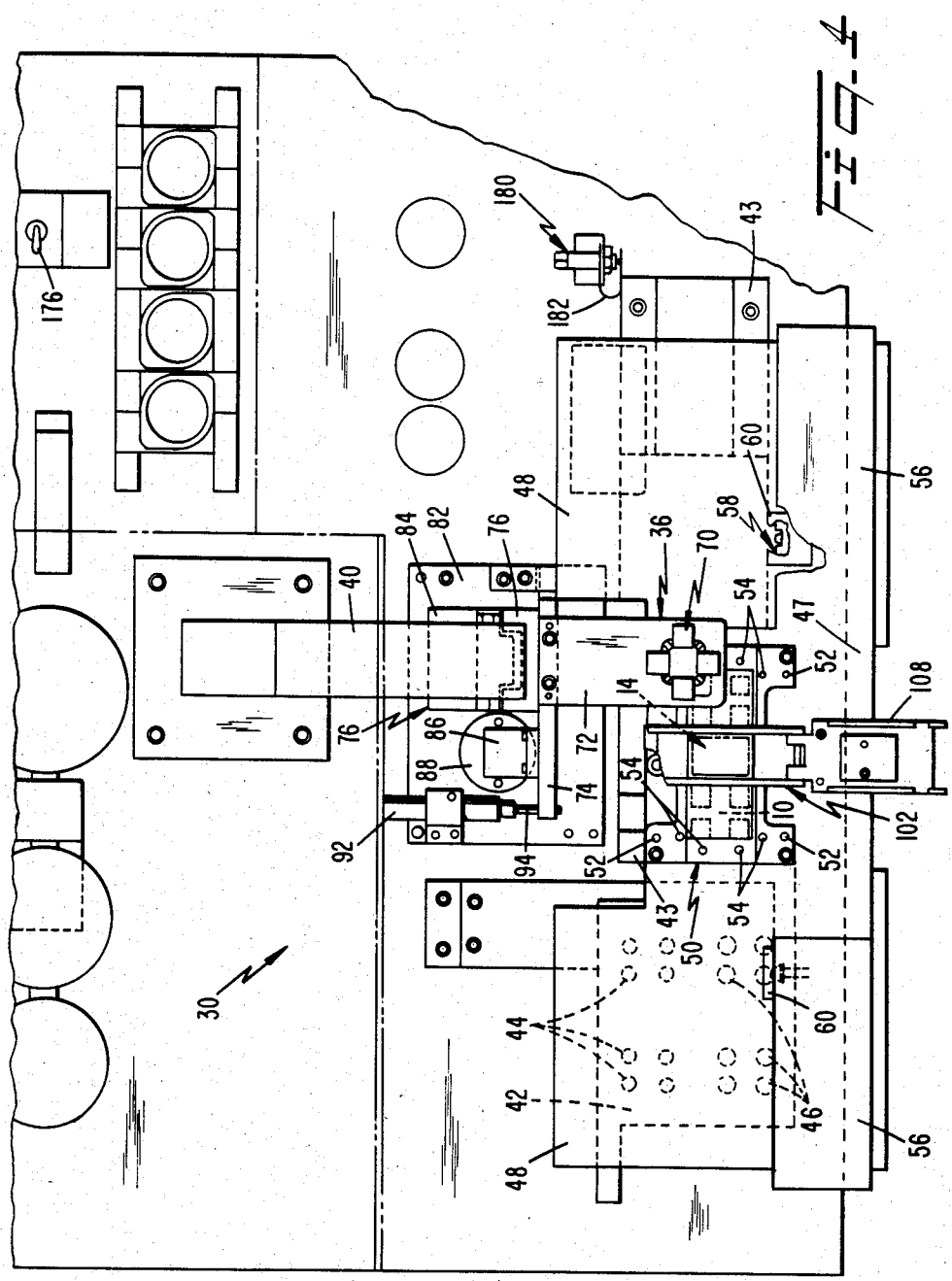

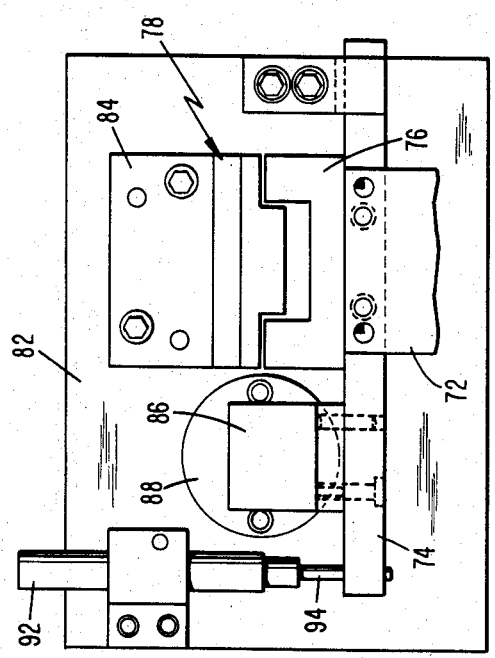
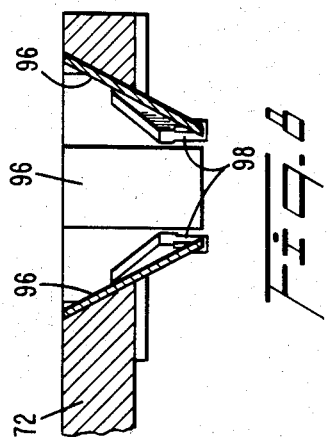
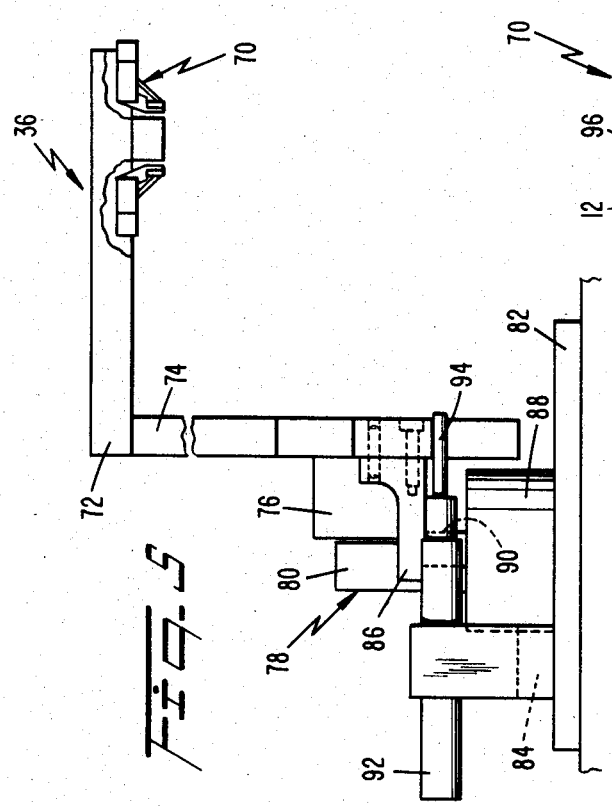
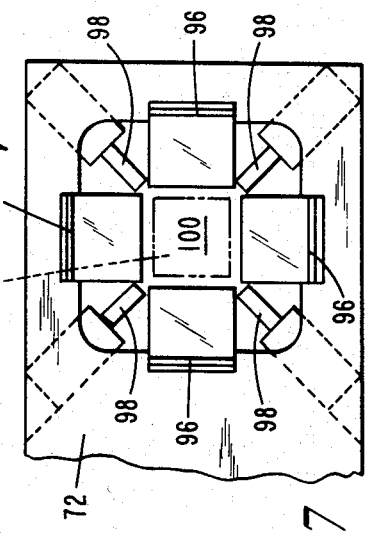

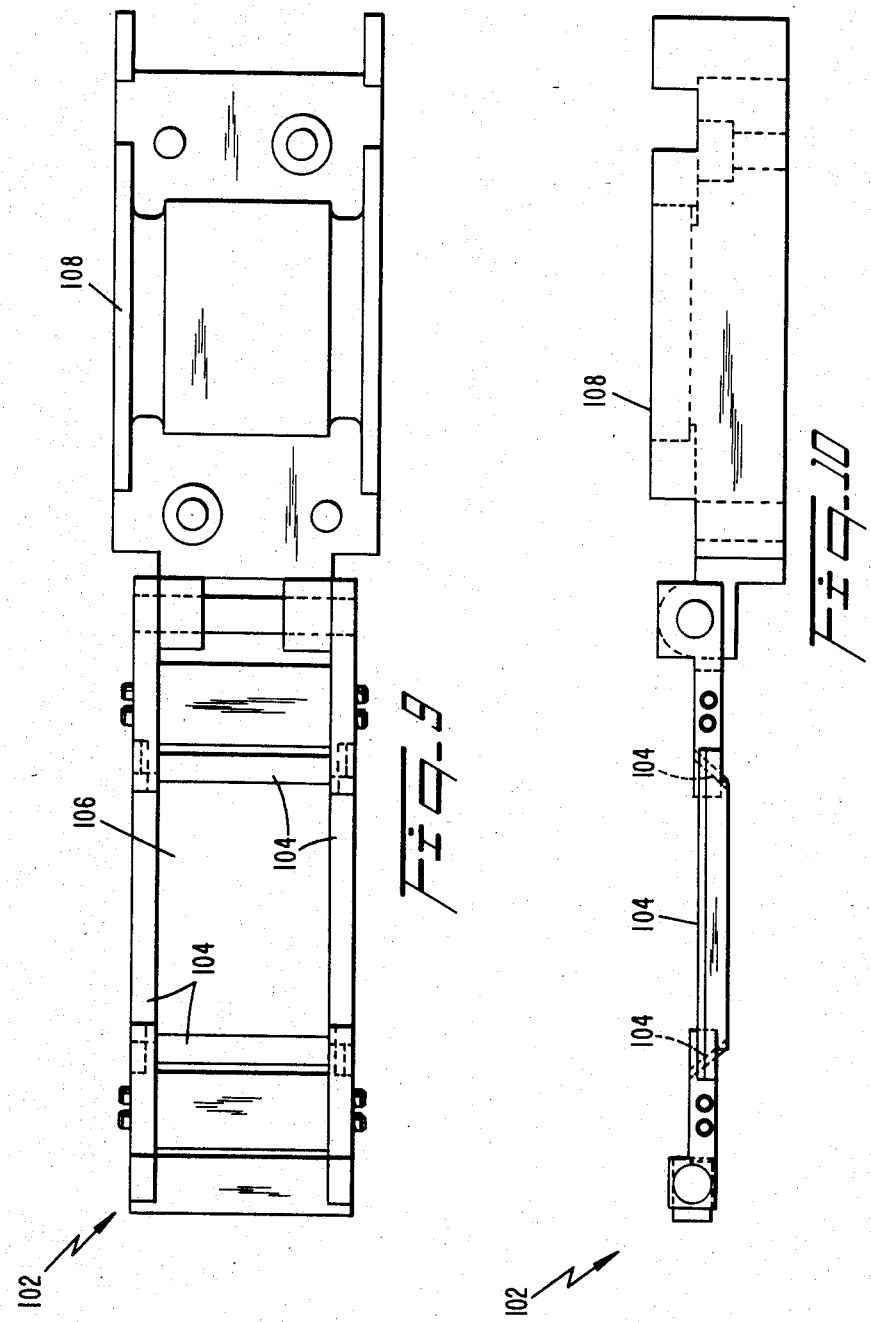

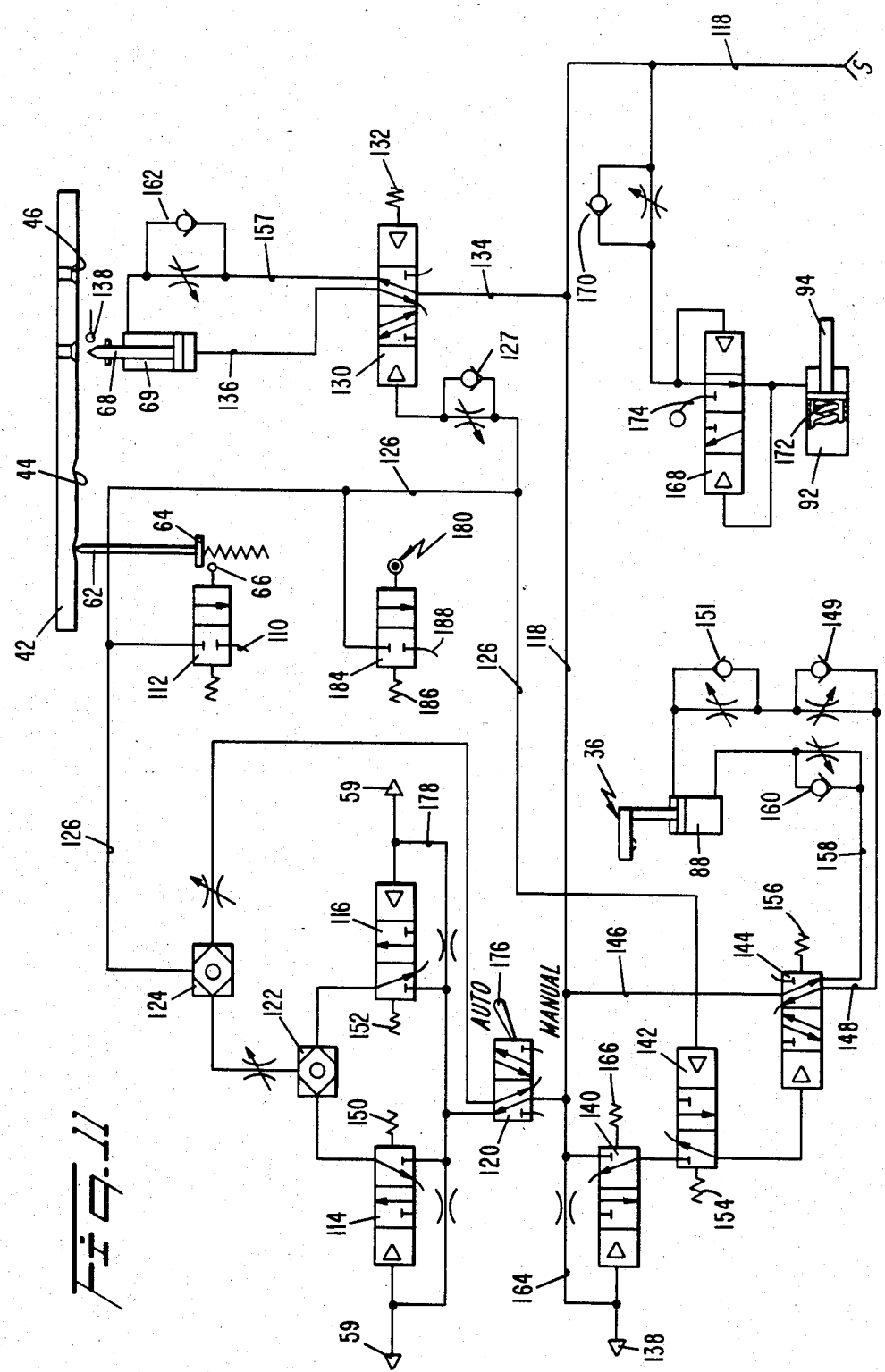

APPARATUS FOR INSPECTING SURFACE MOUNTED COMPONENTS

FIELD OF THE INVENTION

This invention relates to an apparatus for inspecting surface mounted components, and more particularly, to an apparatus for inspecting the solder joints of components mounted on the surface of a ceramic substrate.

BACKGROUND OF THE INVENTION

In the course of manufacture of certain electrical devices, such as hybrid integrated circuits, it is often necessary to mount a plurality of components or chip carriers on one surface of a thin film ceramic substrate. These chip carriers may be attached to the substrate by as many as 32 solder joints. The solder joints, which support the respective chip carriers above the surface of the substrate, establish an air gap between the carriers and the surface of the substrate. The air gap permits the flow of cleaning fluids to remove solder flux that may be present under the chip carriers which would cause leakage currents when high voltages are applied to the substrate. Moreover, the air gap facilitates the encapsulation of the solder joints. The presence of the air gap makes the alignment of the chip carriers with appropriate ceramic substrate pads a difficult task. Thus, each solder joint must be visually inspected for misalignment, shorts between adjacent joints and missing solder joints in order to reduce subsequent costly test diagnostic time of defective circuits.

One method of inspecting the solder joints involves a free-hand rotation of the hybrid integrated circuit beneath a microscope. This method is very cumbersome because each chip carrier must be rotated four times and the location of the defective component or chip carrier must be noted for subsequent repair. This process is difficult to perform without mistakes because the orientation of the circuit is attained by manual manipulation in space. Moreover, it is further complicated by (1) closely spaced adjacent components which block the view of the solder joints or (2) the necessary and repeated steps of looking back and forth between the microscope and documentation which identifies the defective component or chip carrier's location. The process is very time consuming and causes eye fatigue because of the varying focal lengths due to an unsteady hand.

Consequently, an apparatus is needed which can be rapidly operated to accurately fix the orientation of the circuit at a constant focal length from the microscope and allows the inspection of solder joints at varying distances beneath the component or chip carrier.

SUMMARY OF THE INVENTION

The present invention contemplates, among other things, an inspection apparatus having a workholder that is moved to individually precisely position and lock a succession of components mounted on a substrate at an inspection site whereat a viewer is moved to encompass the sides of the component to permit microscopic inspection of the sides and the top surface of the components.

More particularly, the substrate having a pattern of components mounted thereon is loaded onto the workholder. The workholder is then moved so that one of the components is presented at an inspection site. A template, which is secured to the workholder, includes a field of depressions arrayed in a pattern corresponding to the pattern of components and a second field of locator holes arrayed in a pattern corresponding to the patterns of depressions and components. A moveable pin, which is mounted below the template, senses the presence of one of the field of depressions and moves therein upon movement of a component into the exact inspection site. Thereafter, a locator pin moves into one of the field of locator holes in response to the movement of the moveable pin to lock the workholder in a fixed position when one of a pair of switches is activated by an operator. A viewer having mirrors arrayed about an opening of sufficient size to receive the component at the inspection site is moved about the component in order to enable the inspection thereof.

BRIEF DESCRIPTION OF DRAWINGS

Other advantages and features of the invention will be apparent upon consideration of the following detailed description in conjunction with the drawings wherein:

FIG. 1 is a side view showing a hybrid integrated circuit having a plurality of chip carriers and applique circuits mounted thereon;

FIG. 2 is a top view showing a layout of chip carriers and an applique circuit mounted on one major surface of the hybrid integrated circuit of FIG. 1;

FIG. 3 is a side view of an apparatus for inspecting surface mounted components embodying certain principles of the invention;

FIG. 4 is a top view of the apparatus of FIG. 3 having certain parts removed for clarity;

FIG. 5 is a side view showing a viewing assembly having portions cut away to show a viewing adaptor;

FIG. 6 is a top view showing an apparatus for raising the viewing assembly of FIG. 5;

FIGS. 7 and 8 are top and side views, respectively, showing the viewing adaptor of FIG. 5;

FIGS. 9 and 10 are top and side views, respectively, showing an applique viewing adaptor; and FIG. 11 is a schematic view of the pneumatic control system of the apparatus of FIG. 3.

DETAILED DESCRIPTION

Referring to FIGS. 1 and 2, there is shown a hybrid integrated circuit, designated generally by the numeral 10, which includes a plurality of closely-spaced elements, such as components or chip carriers 12 and applique circuits 14 mounted thereon. Additional components (not shown) may be mounted on surface 15 of the applique circuit 14. The hybrid integrated circuit 10 also includes a printed circuit (not shown) formed on major surfaces 16 and 18 of a ceramic substrate, designated generally by the numeral 20. Moreover, a plurality of mounting pads 21 are formed on major surfaces 16 and 18 in order to facilitate the mounting of chip carriers 12 and applique circuits 14 thereon by a plurality of solder joints 22. Sets of leads 24 are mounted along edges 26 and 28 of the ceramic substrate 20 in order to facilitate the mounting of the hybrid integrated circuit 10 into a printed wiring board (not shown). Leads 24 are shown in FIG. 1 as being perpendicular to surfaces 16 and 18. During the inspection of the hybrid integrated circuit 10, leads 24 are parallel to surfaces 16 and 18 and include a carrier (not shown) which is releasably attached to ends of each set of leads positioned along edges 26 and 28.

Referring to FIG. 3, there is shown an apparatus, designated generally by the numeral 30, for inspecting (1) major surfaces 16 and 18 (FIG. 1), (2) solder joints 22 positioned beneath chip carriers 12 of applique circuits 14, (3) lead frames 24 and (4) surface 15 of the applique circuit. Apparatus 30 includes a stage assembly, designated generally by the numeral 32, a positioning or selectively locking assembly, designated generally by the numeral 34, a carrier viewing assembly, designated generally by the numeral 36, and a microscope 38 mounted on a support 40 above the stage and viewing assemblies.

Referring to FIGS. 3 and 4, the stage assembly 32 includes a template 42 mounted for movement on a table 43 mounted for X-Y movement by a commercial X-Y slide arrangement (not shown). The template 42 includes a set of coded representations, such as an array of cone-shaped depressions 44, formed in one surface 45 thereof and which are arranged in a first field such that the positions therein correspond to the positions of the plurality of chip carriers 12 mounted on the substrate 20 (FIGS. 1 and 2). The template 42 also includes an array of apertures or locator holes 46 arranged in a second field so that the positions of the apertures also correspond to the positions of chip carriers 12 mounted on the substrate 20. A platform 47 is positioned above and attached to template 42. A shield 48, which is attached to the platform 47, is positioned between the platform and the template 46. The stage assembly 32 also includes a nest or work holder, designated generally by the numeral 50, which is mounted on platform 47 and supports the hybrid integrated circuit 10 (FIGS. 1 and 2) during an inspection process. The nest 50, which is mounted on platform 47, is moveable in planar fashion during the inspection process. The nest 50 includes four locating posts 52 (three shown) which facilitate the positioning of circuit 10 on the nest. Moreover, the nest 50 also includes position pins 54 which precisely align the leads 24 of circuit 10 on the nest so that the position of the chip carriers 12 correspond to the positions of the array of cone-shaped depressions 44. Handle portions 56, which are also mounted on platform 47, enable an operator to manually shift the stage assembly 32 in X-Y paths beneath the microscope 38. A pair of pneumatic switches, designated generally by the numeral 58, which are mounted on platform 47, enable and control the activation of the positioning assembly 34. Each one of the pneumatic switches 58 includes a nozzle 59 which normally emits a stream of air and which is overlayed by a thin flexible sheet of metal or switch actuator 60, which when flexed acts to close the appropriate one of the nozzles to effectuate operation of the appropriate switch.

Referring again to FIG. 3, the positioning assembly 34 includes a spring-biased sensor plunger 62. The sensor plunger 62, is biased in the direction of the template 42 and is prevented from moving in an upward direction, as viewed in FIG. 3, by under surface 45 of the template. A cam 64, which is positioned on a lower portion of plunger 62, facilitates the operation of a pneumatic switch 66. Depressions 44 allow an upward movement of plunger 62 when positioned thereabove which permit the movement of cam 64 and the closing of switch 66. A cylinder rod or locator pin 68 is activated by air cylinder 69 to move into one of the array of apertures 46 when (1) cam 64 allows switch 66 to close and (2) one of the switch actuators 60 is depressed by an operator. The movement of cylinder rod 68 into one of the array of apertures 46 (1) shifts the template 42 and the stage assembly 32 to precisely center the corresponding one of the chip carriers 12 beneath the carrier viewing assembly 36 when the circuit 10 is mounted in nest 50 and (2) lowers the viewing assembly about the chip carrier.

Referring to FIGS. 3, 4, 5 and 6, the carrier viewing assembly 36 includes a viewing adaptor, designated generally by the numeral 70, mounted on a bracket member 72. Bracket member 72 is coupled to a support member 74 which is coupled to a moveable portion 76 of a roller-bearing slide mechanism 78. A stationary portion 80 of the slide mechanism 78 is fixedly attached to a sub-assembly mounting plate 82 by a first L-shaped bracket 84. A second L-shaped bracket 86, which is secured to support member 74, is positioned above a first air-cylinder 88. When the first air cylinder 88 is activated, cylinder rod 90 engages bracket 86 in order to move the carrier viewing assembly 36 in an upward direction. The carrier viewing assembly 36 also includes a second or lock-out air cylinder 92 having a cylinder rod 94 which is spring biased in an outward direction. Whenever there is a failure in the air supply to air cylinder 92, cylinder rod 94 is forced outward and positions one end thereof beneath bracket 74 in order to lock the viewing assembly 36 in an upward position which prevents the lowering of the viewing assembly. This serves as a safety feature to prevent harm to the integrated circuit 10 should there be a loss of air supply to cylinder 92 while the viewing assembly 36 is in its upward position.

Referring to FIGS. 7 and 8, there is shown an enlarged view of the viewing adaptor 70. The viewing adaptor includes four polished metal mirrors 96 mounted on bracket member 72 at an angle which facilitates the inspection of solder joints 22 (FIG. 1). A plurality of support members or feet 98, which are positioned between the mirrors 96, support the viewing adaptor 70 and limit (1) the downward travel of the viewing assembly 36 (FIGS. 3 and 5) and (2) the contact with hybrid integrated circuit 10 (FIGS. 1, 2, 3 and 4) to four small areas. The mirrors 96 of the viewing adaptor 70 are configured to provide an open center area 100 which (1) provides a target zone or inspection site within which a chip carrier 12 is positioned and (2) enables the operator to inspect lead frames 24 (FIGS. 1 and 2), surfaces 16 and 18 of hybrid integrated circuit 10 and surfaces 15 of the applique circuit 14. When the mirrors 96 are positioned to surround the edges of the selected chip carrier 12, light is impinged on the edges of the carrier and the solder joints 22 under the carrier. A light image of each edge and the solder joints 22 positioned thereby is reflected back onto the respective mirror which may be easily viewed from directly above through the microscope 38.

As noted above, each of the chip carriers 12 has a plurality of solder joints 22 positioned therebeneath. Spacing between the solder joints 22 is very small; thus, the viewing adaptor 70 must enable the operator to inspect each of the solder joints. The angle of the mirrors 96 is set to enable each of the solder joints 22 to be visible as well as a distance beneath the selected chip carrier 12 beyond the tangent of each of the solder joints. Moreover, a portion of the appropriate surface 16 or 18, as well as an adjacent surface of the chip carrier 12, must be visible in order for the operator to determine if an effective connection exists between the substrate 20 and the selected chip carrier.

Referring again to FIGS. 4, 9 and 10, there is shown an auxiliary or applique viewing adaptor, designated generally by the numeral 102, for inspecting the solder joints 22 positioned between the applique circuit 14 (FIGS. 1 and 2) and the respective surfaces 16 and 18 of the hybrid integrated circuit 10. The auxiliary viewing adaptor 102 includes four polished metal mirrors 104 mounted at an angle and positioned to encompass an open center area 106. As is best seen in FIG. 2, solder joints 22 are positioned farther inward from the appropriate edge of the applique circuit 14. Therefore, the angle of mirrors 104 must be such that the solder joints 22 as well as portions of the appropriate surface 16 or 18 are visible. The auxilliary viewing adaptor 102 is pivotally mounted on a support member 108 to permit selective movement of the adaptor about the applique circuit 14 during the inspection thereof. The support member 108 is fixedly attached to platform 47 (FIGS. 3 and 4) adjacent the nest 50.

In operation, and referring to FIGS. 3, 4 and 11, the operator places the hybrid integrated circuit 10 in the nest 50. Grasping the handle portions 56, the staging assembly 32, including the nest 50, is moved to generally position a first chip carrier 12 beneath the microscope 38 within the inspection site. The operator then depresses one or both of the switch actuators 60 to block normal passage of air from the nozzles 59. Spring urged sensor plunger 62 moves upward into one of the depressions 44 as the chip carrier 12 is moved into the inspection site which is indicative of the desired precise positioning of the carrier under the microscope 38. Upward movement of the sensor plunger 62 releases the switch 66 so that air applied to an air valve 112 is blocked from passage through bleed line 110 to the atmosphere. Blockage of one or the other or both of the nozzles 59 causes one or another or both of a pair of associated valves 114 and 116 to shift and in conjunction with the releasing of switch 66 condition an air circuit to the locking cylinder 69.

More specifically, air from source S is impressed over a supply line 118, through a valve 120, through (1) the now shifted valve 114 or 116 or both, (2) the directional valves 122 and 124 to a line 126, and (3) a flow controller 127 to an operator for a valve 130. Valve 130 shifts against the force of a spring 132 to complete an air circuit to the lower end of the air cylinder 69. This air circuit can be traced from supply line 118, over a line 134, through the now shifted valve 130, over a line 136 to the lower end of the air cylinder 69 which reacts to drive the cylinder rod 68 into the aligned aperture 46 to lock the stage assembly 32 and position the chip carrier 12 in a precise inspection location with respect to the microscope 38.

The movement of the cylinder rod 68 into an aligned aperture 46 blocks normal passage of air from nozzle 138. Blockage of nozzle 138 causes air valve 140 to shift to allow the passage of air therethrough. Moreover, air which is impressed over supply line 118, through valve 114 or 116, directional valves 122 and 124, to line 126, is fed to an operator for a valve 142. Valve 142 shifts to permit the flow of air to an operator of an air valve 144 which shifts to complete an air circuit to the upper end of air cylinder 88. This circuit can be traced from supply line 118 over a line 146 through the now shifted valve 144 over a line 148 to the upper end the air cylinder 88 which reacts to retract cylinder rod 90 and enables the lowering of the viewing assembly 36 about the first chip carrier 12.

After the operator has completed the inspection of the solder joints 22 associated with the first chip carrier 12, the switch actuator 60 is released which opens nozzle 59 and permits the normal flow of air therethrough. The flow of air through nozzle 59 causes the associated air valve 114 or 116 to shift due to force of an associated spring 150 or 152, respectively. The shifting of air valve 114 or 116 blocks the flow of air from air supply line 118 to line 126. The blockage of the flow of air to line 126 enables air valve 142 to shift to a closed position due to the force of spring 154 which blocks the flow of air from air supply line 118 through air valve 140 and 142 to the operator of air valve 144. Air valve 144 shifts due to the force of spring 156 to condition an air circuit to the lower end of the air cylinder 88. This air circuit can be traced from supply line 118 over line 146 through now shifted air valve 144 over line 158 through flow controller 160 to the lower end of cylinder 88 which reacts to raise the viewing assembly 36. Moreover, the blockage of air flow to line 126 enables air valve 130 to shift due to the force of spring 132 which completes an air circuit to the upper end of air cylinder 69. This air circuit can be traced from supply line 118, over line 134, through air valve 130, line 157, through flow controller 162 to the upper end of air cylinder 69 which reacts to retract cylinder rod 68 from aperture 46 and unlock the stage assembly 32 for movement to position a second chip carrier 12 beneath the microscope 38. Flow controller 162 is adjusted to insure that the viewing assembly 36 is raised prior to the lowering of the cylinder rod 68 in order to prevent any damage to the circuit 10 which may result if the stage assembly is moved while the viewing assembly 36 is about the chip carrier 12. The lowering of cylinder rod 68 also allows air which flows from supply line 118 over line 164 to bleed through nozzle 138. This allows air valve 140 to shift in a closed position due to spring 166.

An additional feature of the fixture 30 enables the operator to speed up the inspection process by activating one or both of the switches 58 while searching for the location of one of the chip carriers 12. As noted above, the cylinder rod 68 is raised into one of the apertures 46 only when sensor plunger 62 enters into one of the depressions 44. Thus, the operator may freely and rapidly move the stage assembly 32 with one or both of the switches 58 activated and the cylinder rod 68 will only be raised when one of the apertures 46 is positioned above it. Moreover, the viewing assembly 36 will be lowered only after the cylinder rod 68 has entered one of the apertures 46 and has blocked the bleeding of air from nozzle 138.

After the operator has completed the inspection of the solder joints 22 for all of the chip carriers 12, the switch actuator 60 is again released which permits air which flows from supply line 118 through air valve 120 to bleed through nozzles 59. As noted above, the viewing assembly 36 is raised before the cylinder rod 68 is lowered which enables the operator to freely move the stage assembly 32. The operator then moves the stage assembly 32 so that the auxiliary viewing adaptor 102 can be moved about the applique circuit 14. As is best seen in FIG. 2, the size of the applique circuit 14 is much larger than that of the chip carriers 12. Moreover, the applique circuit 14 is larger than the field of view of the microscope 38; thus, the stage assembly 32 must be indexed by the operator in order to present groups of the solder joints 22 associated with the applique circuit to the inspection site for inspection until all of the solder joints have been inspected. During this inspection, the viewing assembly 36 is held in its upward position, as seen in FIGS. 5 and 6, due to the absence of any cone-shaped depressions 44 in this area of the template 42 thus causing cam 64 to exert pressure on switch 66 which prevents the operator from activating either of the pair of switches 58.

Lock-out cylinder 92 is also coupled to air line 118 through air valve 168 and flow controller 170. As noted above, cylinder 92 is spring-biased in an outward direction. Thus, air from source S is impressed over supply line 118 through flow controller 170 to an operator of an air valve 168 which causes the air valve to shift to condition an air circuit to an upper end of cylinder 92. This air circuit enables the cylinder rod 94 to be retracted against the force of spring 172 contained within cylinder 92. When there is a loss of air pressure in line 118 due to a failure of air from source S, air valve 168 is allowed to change its position due to air pressure within an opposite operator associated with cylinder 92. As air valve 168 changes its position, air pressure from cylinder 92 leaks out through line 174 which permits the plunger to be extended as a result of spring 172 within cylinder 92 and positions itself under an end of bracket 74 to hold the viewing assembly 36 in its upward position.

Apparatus 30 can be also utilized to inspect lead frames 24 mounted along edges 26 and 28 of the ceramic substrate 20 by positioning the appropriate edge 26 or 28 beneath the microscope 38. As noted above, the same safety feature which prevents the lowering of the viewing assembly 36 is in effect during the inspection of the lead frames 24.

Apparatus 30 also includes a maintenance switch 176 which enables the operator to operate the fixture without activating the switch actuator 60 during a maintenance operation. When switch 176 is placed in an automatic (auto) position, as seen in FIG. 11, the operator must activate switch actuators 60 which condition an air circuit to line 126. This air circuit can be traced from air supply line 118 through air valve 114 or 116, directional flow controllers 122 and 124 and into line 126. When switch 176 is placed in a manual position, an air circuit is conditioned to line 126 which by-passes air valves 114 and 116 and directional flow controller 122. This air circuit can be traced from air supply line 118 through the now shifted air valve 120 over line 128 and into line 126.

Apparatus 30 also includes a switch, designated generally by the numeral 180, that prevents the operator from lowering the viewing assembly 36 by activating switches 58 when the stage assembly 32 is moved to a loading position, wherein the stage is moved to the extreme right of the microscope 38 for loading the hybrid integrated circuit 10 onto nest 50. Switch 180 includes a switch actuator 182, which is engaged by the table 43 when the stage assembly 32 is in the loading position and which causes an air valve 184 to shift against the force of a spring 186 so that air applied to the valve bleeds through line 188. If the operator activates switches 58, air valves 114 or 116, or both, are shifted and completes a circuit from line 118 to line 126. Air from source S is now impressed over line 118, through the now shifted air valves 114 or 116, through directional flow controller 122 and 124, over line 126 and bleeds out through line 188 which prevents the operation of (1) air valve 130 which enables the operation of air cylinder 69 and (2) air valve 142 which enables the operation of air cylinder 88. Therefore, even though the operator has activated switches 58, air cylinder 69 is not operated to lock and position the stage assembly 32 and the viewing assembly 36 is not lowered when the stage assembly is in the loading position.

What is claimed:

1. An apparatus for precisely positioning and inspecting an array of elements positioned on a base member, which comprises:

a table mounted for X-Y movement;

a workholder for supporting the base member movable with said table in planar fashion relative to an inspection site;

a template mounted on the table and secured to said workholder and including coded representations indicative of the positions of the elements on the base member, said representations being formed on an under surface of the template;

selectively operable means for locking said workholder to position an element at the inspection site;

a spring-biased sensor plunger positioned beneath the template and biased toward the under surface thereof for sensing the coded representations;

a cam mounted on a lower portion of the sensor plunger and moveable therewith for engaging and operating a switch to generate a signal indicating that an element is at the inspection site;

means operated by said signal for operating said selectively operable means to lock said workholder with the element at the inspection site;

visual inspection means mounted for movement toward and away from the inspection site; and means responsive to the operation of said locking means for moving said visual inspection means to the inspection site.

2. The apparatus as recited in claim 1 wherein the visual inspection means includes a plurality of mirrors arrayed about an opening of sufficient size to receive one of the array of elements.

3. The apparatus as recited in claim 2 which further includes a pair of switches mounted on the workholder and actuable in cooperation with said generated signal for operating said locking means.

4. The apparatus as recited in claim 3 wherein the template includes an array of apertures arranged in a field so that positions of the apertures correspond to the positions of the elements positioned on the base member and wherein the locking means includes an air cylinder having a cylinder rod which is positioned beneath the array of apertures for movement into an aligned one of the apertures, and means responsive to the signal generated by the generating means and the activating of at least one of the pair of switches for operating said air cylinder and moving said cylinder rod into the aligned aperture.

5. An apparatus for inspecting a pattern of components mounted on a substrate, which comprises:

a workholder for receiving the substrate;

means for moving said workholder to selectively present each component to an inspection site;

a template secured to said workholder and having a first field of depressions arrayed in a pattern corresponding to the pattern of components and a second field of locator holes arrayed in a pattern corresponding to the patterns of depressions and components;

a pair of switches mounted on the moving means;

means including a moveably mounted plunger for sensing the field of depressions and moveable into a depression upon movement of a component into the inspection site;

a moveably mounted locator pin;

means responsive to the movement of said sensing plunger into a depression and the activation of at least one of the pair of switches for moving said locator pin into a locator hole to lock said workholder with a component at the inspection site;

a viewer with mirrors arrayed about an opening;

means mounting said viewer for movement to position said mirrors about a component at the inspection site; and means rendered effective by movement of said locator pin into one of said locator holes for moving said viewer to position said mirrors about the component at the inspection site.

6. The apparatus as recited in claim 5 wherein an applique circuit is also mounted on the substrate and which further comprises:

an auxiliary viewing adaptor which includes a plurality of mirrors arrayed about an opening of sufficient size to receive the applique circuit; and means mounting said auxiliary viewing adaptor for pivotal movement to position said mirrors about the applique circuit presented at the inspection site by the moving means.

7. The apparatus as recited in claim 5 wherein the components are mounted on the substrate so that an air gap is created by a plurality of solder joints positioned between adjacent major surfaces of the substrate and the components and wherein the mirrors are mounted at an angle such that portions of the major surfaces, the plurality of solder joints and distance beyond the tangent of each of the solder joints are visible through the viewer.

* * * * *